United States Patent [19]
Phillips

[11] Patent Number: 5,458,656
[45] Date of Patent: Oct. 17, 1995

[54] ENERGY-STORING PROSTHESIS LEG PYLON VERTICAL SHOCK LEG

[75] Inventor: Van L. Phillips, Rancho Santa Fe, Calif.

[73] Assignee: Flex-Foot, Aliso Viejo, Calif.

[21] Appl. No.: 171,244

[22] Filed: Dec. 20, 1993

Related U.S. Application Data

[63] Continuation of Ser. No. 91,473, Jul. 14, 1993, abandoned, which is a continuation of Ser. No. 940,768, Sep. 4, 1992, abandoned, which is a continuation of Ser. No. 767,679, Sep. 30, 1991, abandoned.

[51] Int. Cl.$^6$ .................................. A61F 2/62; A61F 2/66
[52] U.S. Cl. ................................ 623/27; 623/52; 623/53; 623/38
[58] Field of Search .................................. 623/38, 47–52, 623/27, 53; 403/166, 82, 109, 166

[56] References Cited

U.S. PATENT DOCUMENTS

| | | |
|---|---|---|
| 49,528 | 8/1865 | Jewett ........................................ 623/33 |
| 61,780 | 2/1867 | Watson . |
| 65,187 | 5/1867 | Emery . |
| 277,562 | 5/1867 | Furrer . |
| 366,494 | 7/1887 | Marks . |
| 693,400 | 2/1902 | Jachimsen . |
| 708,685 | 9/1902 | White . |
| 809,875 | 1/1906 | Wilkins . |
| 817,340 | 4/1906 | Rosenkranz . |
| 827,720 | 8/1906 | Erwin . |
| 951,989 | 3/1910 | Hanger . |
| 1,071,230 | 8/1913 | Hanger . |
| 1,103,828 | 1/1913 | Thomas . |
| 1,128,018 | 2/1915 | McFarland . |
| 1,151,144 | 8/1915 | Wofe et al. . |
| 1,294,632 | 2/1919 | Dickson . |
| 1,352,943 | 9/1920 | Dodge . |
| 1,424,264 | 8/1922 | Shrodes ..................................... 623/52 |
| 1,804,915 | 5/1931 | Collins . |

(List continued on next page.)

FOREIGN PATENT DOCUMENTS

| | | |
|---|---|---|
| 0179844 | 10/1954 | Austria ..................................... 623/38 |
| 25322 | 10/1972 | France . |
| 2501999 | 9/1982 | France ..................................... 623/38 |
| 2567395 | 1/1986 | France ..................................... 623/27 |
| 0605613 | 5/1978 | U.S.S.R. .................................. 623/51 |
| 1465046 | 3/1989 | U.S.S.R. .................................. 623/47 |
| 22172 | of 1898 | United Kingdom . |
| 16750 | 12/1916 | United Kingdom . |
| 120462 | 11/1918 | United Kingdom . |
| 275902 | 8/1927 | United Kingdom . |
| 621576 | 7/1946 | United Kingdom . |
| 120445 | 10/1972 | United Kingdom . |
| 1371996 | 10/1974 | United Kingdom . |
| 1432481 | 4/1976 | United Kingdom . |
| 2092451 | 2/1982 | United Kingdom . |
| 2124493 | 2/1984 | United Kingdom . |
| 8800815 | 7/1986 | WIPO . |
| 8905617 | 12/1987 | WIPO . |
| 8909036 | 10/1989 | WIPO . |

OTHER PUBLICATIONS

"The Seattle Prosthesis Foot—A Design for Active Sports: Preliminary Studies," E. M. Burgess, M. D., et al., *Orthotics and Prosthetics Journal*, vol. 37, No. 1, Spring 1983.
The Seattle Foot—Winner of Presidential Design Awards—Jan. 20, 1985.
Copes/Bionic Ankle.
*L. A. Times* View Section, "Seattle Foot," Jun. 12, 1984.
Campbell Childs, Jr. Product Catalog.

*Primary Examiner*—David H. Willse
*Attorney, Agent, or Firm*—Knobbe, Martens, Olson & Bear

[57] ABSTRACT

A prosthetic leg and pylon is characterized by upper and lower pylon members having one or more spring elements operatively attached or disposed therebetween. The pylon members are preferably interengaged and reciprocable one on the other, so that forces imposed on the pylon result in such reciprocation and the corresponding storage of energy in the spring element or elements. The spring elements are capable of releasing some of the stored energy upon removal of the force. Constraining bands may be utilized to limit the amount of deflection of the elongated springs, and the effective length of the prosthesis may be readily adjusted.

28 Claims, 5 Drawing Sheets

U.S. PATENT DOCUMENTS

| | | |
|---|---|---|
| 2,075,583 | 3/1937 | Lange . |
| 2,126,654 | 8/1938 | Morris . |
| 2,379,538 | 7/1945 | Meierhofer . |
| 2,440,075 | 4/1948 | Campbell . |
| 2,453,969 | 11/1948 | Carter . |
| 2,480,856 | 9/1949 | Henschke et al. ............... 623/26 |
| 2,543,908 | 3/1951 | Guzey . |
| 2,556,525 | 6/1951 | Drennon . |
| 2,570,735 | 10/1951 | Weise . |
| 2,619,652 | 12/1952 | Vesper . |
| 2,692,392 | 10/1954 | Bennington et al. ............ 623/38 X |
| 2,699,554 | 1/1955 | Comelli . |
| 2,899,685 | 8/1959 | Bourcier de Carbon . |
| 3,335,428 | 5/1967 | Gajdos . |
| 3,400,408 | 9/1968 | Garcia . |
| 3,438,587 | 4/1969 | Jackson . |
| 3,659,294 | 5/1972 | Glabiszewski . |
| 3,663,967 | 5/1972 | Vermillion ...................... 623/38 X |
| 3,707,731 | 1/1973 | Morgan . |
| 3,754,286 | 8/1973 | Ryan . |
| 3,833,941 | 9/1974 | Wagner . |
| 3,874,004 | 4/1975 | May . |
| 3,889,301 | 6/1975 | Bonner, Sr. . |
| 3,890,650 | 6/1975 | Prahl . |
| 3,953,900 | 3/1976 | Thompson . |
| 4,007,496 | 2/1977 | Glabiszewski . |
| 4,074,542 | 2/1978 | Hankosky et al. ............... 403/166 X |
| 4,089,072 | 5/1978 | Glabiszewski . |
| 4,091,472 | 5/1978 | Daher et al. . |
| 4,128,903 | 12/1978 | Marsh et al. . |
| 4,161,042 | 7/1979 | Cottingham et al. . |
| 4,177,525 | 12/1979 | Arbogast et al. . |
| 4,180,872 | 1/1980 | Chaikin . |
| 4,186,449 | 2/1980 | Horvath . |
| 4,216,550 | 8/1980 | Thompson ...................... 623/38 X |
| 4,225,982 | 10/1980 | Cochrane et al. . |
| 4,268,922 | 5/1981 | Marsh et al. . |
| 4,306,320 | 12/1981 | Delp . |
| 4,314,398 | 2/1982 | Pettersson . |
| 4,328,594 | 5/1982 | Campbell et al. . |
| 4,360,931 | 11/1982 | Hampton . |
| 4,370,761 | 2/1983 | Serri . |
| 4,395,783 | 8/1983 | Eyre et al. . |
| 4,397,048 | 8/1983 | Brown et al. . |
| 4,459,709 | 7/1984 | Leal et al. . |
| 4,506,395 | 3/1985 | Haupt . |
| 4,536,898 | 8/1985 | Palfray . |
| 4,619,661 | 10/1986 | Axelsson . |
| 4,636,220 | 1/1987 | Ziegelmeyer . |
| 4,652,266 | 3/1987 | Truesdell . |
| 4,721,510 | 1/1988 | Cooper et al. . |
| 4,728,336 | 3/1988 | Cooper . |
| 4,792,340 | 12/1988 | Aulie et al. . |
| 4,865,612 | 9/1989 | Arbogast et al. . |
| 4,883,493 | 11/1989 | Martel et al. .................. 623/38 |
| 4,883,494 | 11/1989 | Cooper . |
| 4,892,553 | 1/1990 | Prahl . |
| 4,892,554 | 1/1990 | Robinson . |
| 4,911,724 | 3/1990 | Fikes . |
| 4,923,475 | 5/1990 | Gosthnian et al. . |
| 4,938,777 | 7/1990 | Mason et al. . |
| 4,959,073 | 9/1990 | Merlette . |
| 4,969,911 | 11/1990 | Greene . |
| 4,972,920 | 11/1990 | Zamitter et al. ................ 180/227 |
| 4,994,086 | 2/1991 | Edwards . |
| 5,004,477 | 4/1991 | Palfray . |
| 5,007,938 | 4/1991 | Prahl . |
| 5,013,325 | 5/1991 | Rennerfelt . |
| 5,019,109 | 5/1991 | Voisin . |
| 5,037,444 | 8/1991 | Philips . |
| 5,062,859 | 11/1991 | Naeder . |
| 5,066,306 | 11/1991 | Firth . |
| 5,071,435 | 12/1991 | Fuchs et al. .................... 623/16 |
| 5,108,454 | 4/1992 | Rothschild et al. . |
| 5,112,356 | 5/1992 | Harris et al. . |
| 5,116,381 | 5/1992 | Palfray . |
| 5,116,384 | 5/1992 | Wilson et al. . |
| 5,116,385 | 5/1992 | Allard et al. . |
| 5,156,631 | 10/1992 | Merlette . |
| 5,156,632 | 10/1992 | Wellershaus . |

ENERGY-STORING PROSTHESIS LEG PYLON VERTICAL SHOCK LEG

This application is a continuation of application Ser. No. 08/091,473, filed Jul. 14, 1993, now abandoned, which is a continuation of application Ser. No. 07/940,768, filed Sep. 04, 1992, now abandoned, which is a continuation of application Ser. No. 07/767,679, filed Sep. 30, 1991, now abandoned.

BACKGROUND OF THE INVENTION

This invention relates to leg prostheses in general, and specifically to a pylon-which is capable of storing and subsequently releasing energy during use of the prosthesis. The pylon of the invention is characterized by a lightweight construction, and preferably may be modified and adjusted to accommodate an individual wearer's needs and particular uses.

Moreover, the pylon of the invention may be utilized in connection with any of a broad selection of prosthetic sockets for attachment to the wearer, as well as in connection with any of a broad selection of prosthetic feet attached to, or integrally formed with, the lower end of the pylon.

Various types of foot and leg prosthetic devices are known in the prior art. Such devices generally include some form of attachment for coupling the device to the dorsal end of the limb and for extending to the ground to provide body support. Moreover, these devices generally constitute attempts to simulate the structure and/or the performance of the human leg and foot.

Among the features desirable in leg and foot prostheses is the incorporation of some means for storing and releasing energy during use of the prosthesis; for example, during ambulation. Such energy performance permits the wearer to expend less energy and to participate in activities not otherwise feasible to the wearer. Consequently, the wearer becomes less tired, is able to perform for longer periods of time. In many ways, energy-storing and releasing prostheses remove barriers and limitations which might otherwise restrict the wearer's activities. Examples of prostheses which provide energy storage and release are set forth in U.S. Pat. No. 4,547,913 for my invention relating to a "Composite Prosthetic Foot and Leg", U.S. Pat. No. 4,822,363 for my invention relating to a "Modular Composite Prosthetic Foot and Leg", and U.S. Pat. No. 5,037,444 for my invention relating to a "Prosthetic Foot".

Although the benefits and desirability of energy storage and release in prosthetic devices is known, no prior art prosthetic devices provide those benefits in the relatively simple construction set forth in my present invention, which is adaptable to wide variety of applications, is readily manufacturable and adjustable, and permits an extremely sensitive energy performance.

In addition, and as indicated above, my present invention is compatible with a wide range of prosthetic feet and legs and enhances the performance of such devices. Examples of such prosthetic foot devices include U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

Some of the benefits of my inventions disclosed in my aforementioned patents inhere in the interchangeable, lightweight construction which provides selectable degrees of strength and flexibility in a given structure. My present invention preferably permits similar interchangeability, providing additional or alternative control and adjustability of the performance of the prosthesis. Moreover, my present invention provides some degree of those adjustability and performance benefits to wearers of otherwise conventional or non-energy-storing prosthetic devices.

OBJECTS AND ADVANTAGES OF THE INVENTION

It is, therefore, an object of my invention to provide an energy-storing prosthetic pylon which may be incorporated in a prosthetic leg. The pylon preferably includes upper and lower pylon members connected by energy-storing means such as one or more elongated spring elements. The pylon members are preferably overlappingly interengaged and reciprocable one on the other. This interengagement of the upper and lower pylon members may be accomplished, for example, through the provision of an interfitting, slidably disposed sleeve and arm configuration for the pylon members. In the preferred embodiment, forces imposed on the pylon cause the aforesaid reciprocation of the pylon members and the corresponding storage of energy in the spring element or elements.

Among other things, the interengagement of the upper and lower pylon members assists in maintaining appropriate alignment of the pylon during use. Notably, such alignment may include one or more dynamic components; for example, in addition to the energy-storing compression which is one of the primary functions of the pylon, the alignment of the pylon members may permit rotation of "toe-in" and/or "toe-out" during use, such as is accomplished by known prosthetic "rotators". In other words, during use by the wearer, the preferred embodiment of the invention permits a desired and determinable amount of rotation of the lower end of the pylon with respect to the wearer's socket. Such rotation is beneficial, and simulates the action of a natural human knee/ankle, in a number of activities that involve the twisting of a person's body with respect to their planted foot, such as golf, tennis, and the like.

The pylon is characterized by an upper extremity adaptable for securement to the wearer's limb and a lower extremity adaptable for securement to a prosthetic foot, with the aforesaid energy-storing means such as one or more elongated spring elements interconnecting or acting between the two extremities. In the preferred embodiment, the specific interconnection of the spring elements to the pylon extremities is preferably of a pivoting nature. Such a pivoting structure eliminates or greatly reduces the stress concentrations that would otherwise be present during compression of the pylon and spring elements. Non-pivoting interconnection of the spring to the pylon members could, of course, be utilized without departing from the teachings of the invention. When such pivoting structures are utilized, however, it is preferable to minimize the friction inherent in such a pivot. Any friction which occurs in the pivoting action results in a loss energy which could otherwise be stored in the energy storage means and subsequently released beneficially to the amputee. A preferred method of minimizing this friction loss is to coat contacting surfaces with TEFLON® coating or similar material, as discussed herein.

The particular selections of a device for attachment to the wearer and of a prosthetic foot may be permanently or demountably associated with the pylon. Demountable association permits one or more of the socket, the pylon, and/or the leg and foot prostheses components to be readily exchanged with correspondingly constructed elements to provide size adjustment and/or different energy-performance characteristics to suit the size of leg and foot of the amputee or the stride, height, weight, and activity level of the amputee. Therefore, a range of combinations of spring rate and size can be provided to the amputee. Moreover, manufacture and inventory costs are reduced because prostheses appropriate for amputees of greatly differing heights and weights can be assembled from a relatively small inventory of "standard" sized components.

Another object of the invention is the provision of a prosthetic pylon of the aforementioned character in which the energy-storing means such as one or more spring elements is fabricated from laminates, chopped fiber and/or other material maintained in operative relationship by an encapsulating polymer such as a thermosetting or thermoplastic resin.

A further object of the invention is the provision of a prosthetic pylon of the aforementioned character which includes upper and lower interengagable, relatively reciprocatable pylon members and energy storage means connected or operably disposed therebetween to maintain said lower member in an extended position relative to said upper member, whereby when a contact-generated compressive force is impressed upon the lower member, it will be reciprocated relatively to said upper member to compress the energy storage means into an energy storage mode, and when said force is released the storage means will urge the lower member to its extended position.

Another object of the invention is the provision of the aforesaid prosthetic pylon, in which a multiplicity of said spring elements may be utilized in combination with each other to vary the resistance of the prosthesis to loads imposed thereupon. The concept of the multiplicity of spring elements includes the provision of spring elements characterized by different spring rates, which permits the resistance of the total combination to deflection to be precisely adjusted to the weight, activity level and other characteristics of the individual for whom said pylon is being adjusted.

Still another object of my invention is the provision of a prosthesis of the aforementioned character in which the energy storage and release means includes one or more members fabricated from rubber or a rubber-like material. Such rubber spring members may be utilized in connection with or instead of the aforementioned elongated spring elements.

Yet another object of my invention is the provision of a prosthesis of the aforementioned character having elongated spring elements and further including constraining means such as, for example, an elastic cord for constraining the amount of deflection of the one or more elongated spring elements. Such constraining means provide an additional means to "fine-tune" the energy performance of the prosthesis.

In order to impart a cosmetic aspect to the prosthetic leg, after proper fitting of the leg to insure that it is properly balanced and of appropriate size, the prosthesis may be encapsulated in a suitably shaped cosmetic shroud. The shroud must be sufficiently flexible so as not to inhibit the free movement and flexure of the leg, but, because of the inherently resilient and stress-absorbing characteristics of said leg, little or no dependence is needed upon the ancillary cushioning action of the shroud. Moreover, the shroud should accommodate any desired flexure of the energy-storage means without incurring damage or undesirably restricting such flexure.

Consequently, prosthetists and wearers will be able to adjust the flexibility of the pylon at their discretion. Through the provision of preferably demountable, adjustable attachment means such as gripping clamps for attaching the prosthetic foot to the pylon, the pylon of my invention may be provided in standard lengths but still be readily "custom-fitted" to a wide range of effective lengths.

Other objects and advantages of the invention will be apparent from the following specification and the accompanying drawings, which are for the purpose of illustration only.

BRIEF DESCRIPTION OF THE DRAWINGS

18—18 of FIG. 17; and

DESCRIPTION OF PREFERRED EMBODIMENT

Figures 1, 2, 5:
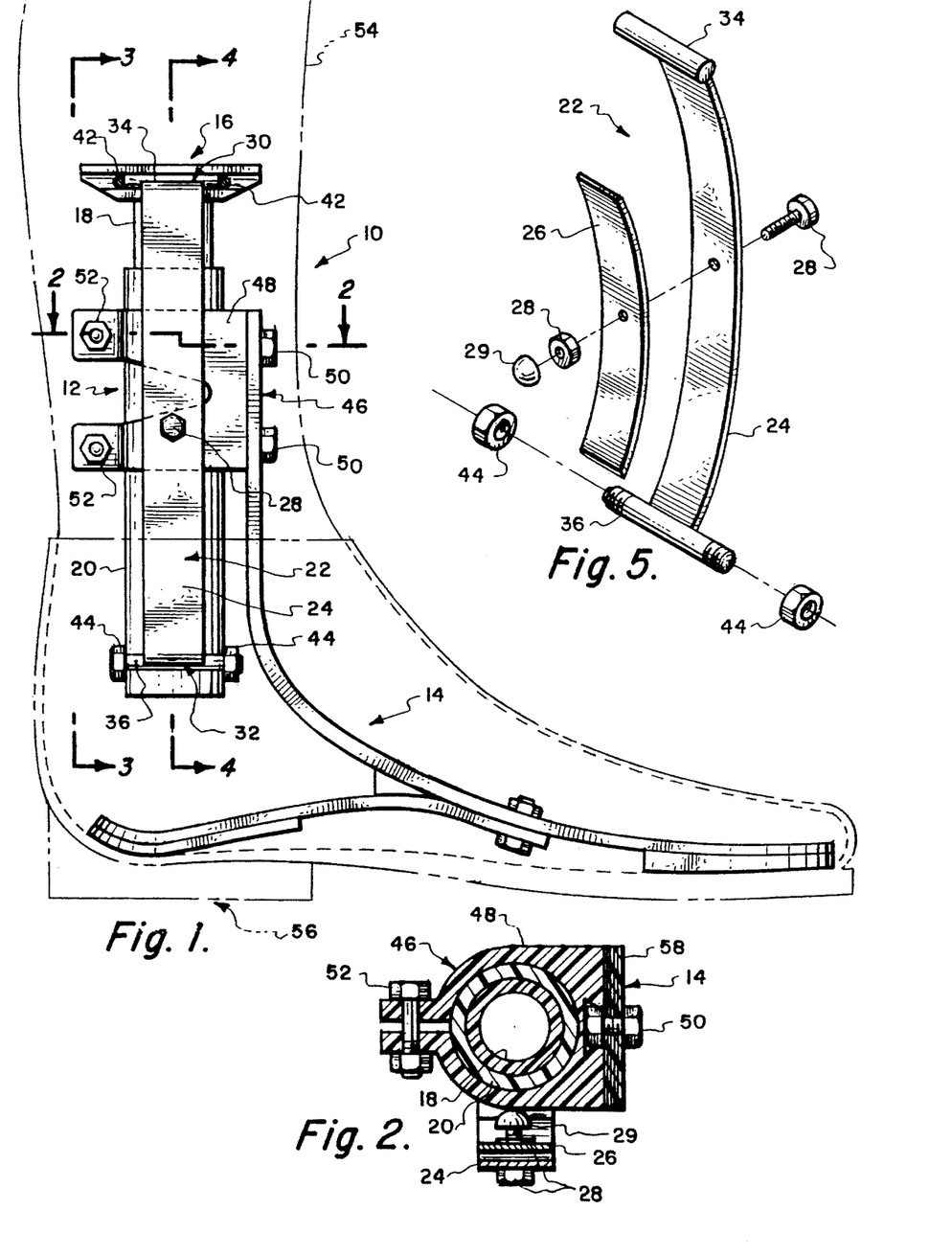
FIG. 1 is a side elevation view of a preferred embodiment of a prosthesis constructed and assembled in accordance with the teachings of the invention.
FIG. 2 is a sectional view, taken along line 2—2 of FIG. 1.
FIG. 5 is an exploded view of a preferred embodiment of spring elements utilizable in the invention.

Referring to the drawings, and particularly to FIG. 1 thereof, I show a lower leg prosthesis 10 constructed and assembled in accordance with the teachings of the invention and including a prosthetic pylon 12. For purposes of illustration, the prosthesis 10 is shown as including a prosthetic foot 14 and as having an attachment means 16 at an upper end thereof for operatively attaching the prosthesis 10 to a wearer, through the use of a socket or other expedient (illustrated, by way of example, as the socket 90, FIGS. 17 and 19).

Figure 3:
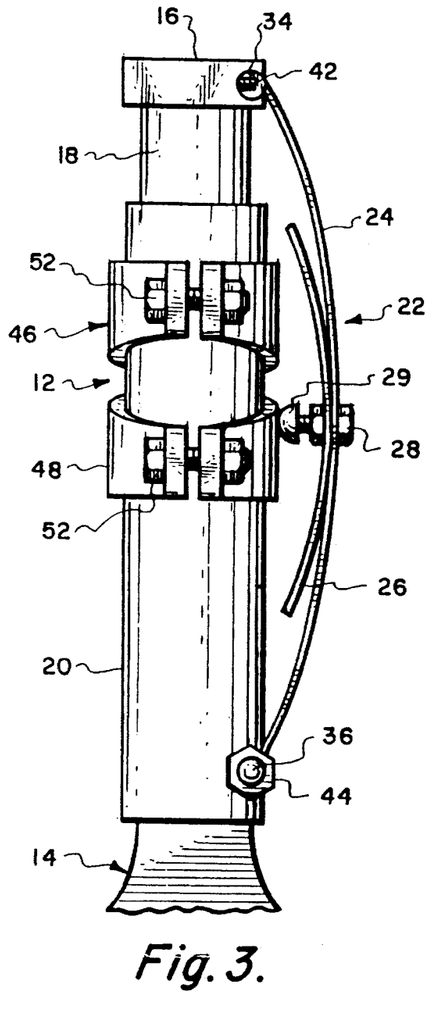
FIG. 3 is a partial rear elevation view, taken along line 3—3 of FIG. 1.
Figure 4:
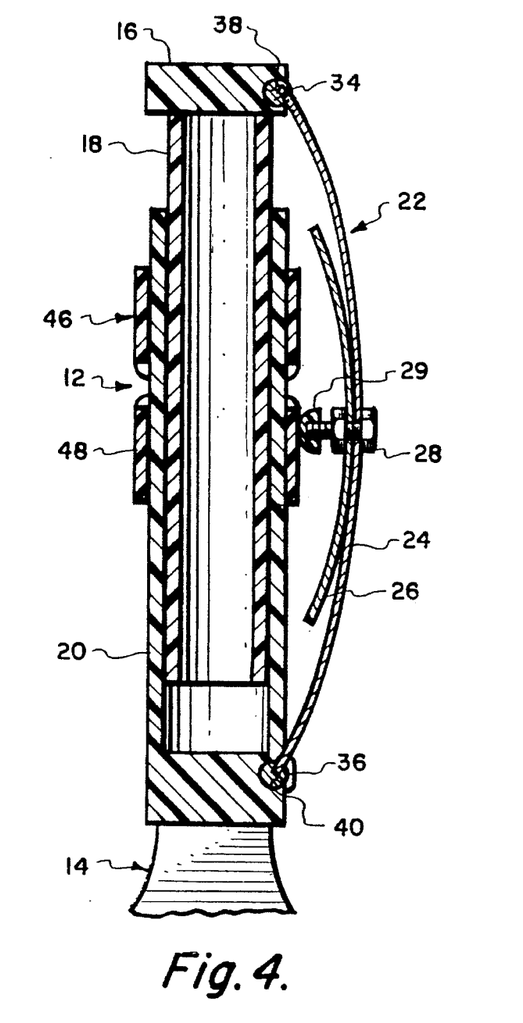
FIG. 4 is a partially sectional rear view, taken along line 4—4 of FIG. 1.

In the preferred embodiment, and as best shown in FIGS. 3 and 4, the pylon 12 includes pylon means having a first portion constituting an upper member 18 and a second portion constituting a lower member 20. As shown in the drawings, these first and second portions are preferably slidingly and reciprocably interengaged with each other in the manner of a sleeve member and an arm member, while retaining their operative horizontal alignment with each other through a relatively close fit between the outside dimensions of the member 18 and the inside dimensions of the lower member 20.

Although the upper and lower members 18 and 20 are illustrated and described as being circular and tubular and coaxially aligned with each other, those skilled in the art will understand that a wide variety of shapes, sizes and alignment patterns may be utilized with efficacy without departing from the scope of the invention. By way of example, but not by way of limitation, the upper and lower members 18 and 20 may have cross-sections which are square (see FIGS. 11 and 12), rectangular, or D-shaped (see FIG. 12A), or may be solid instead of hollow (see, for example, member 76 of FIG. 15).

Additionally exemplary of the variety of configurations of the pylon members is FIG. 6, discussed below, in which the lower portion 20 may be disposed on the interior of the upper portion 18. In such an embodiment, the respective upper and lower portions must be of sufficient length to otherwise permit the desired unimpeded reciprocation of the prosthesis, as described below.

Moreover, the cylinders 18 and 20 are preferably fabricated from composites of fiber and resin, similar to the prostheses described in my above-listed patents. Such fibers may include, for example, carbon graphite, fiberglass, Kevlar or a similarly strong, light-weight material. The fiber may be in laminated or chopped form. These fibers are preferably retained in the desired operative configuration by polymer impregnation of a thermoplastic or thermosetting resin, such as epoxy, polyester, vinylester, polyethylene or polypropylene. Less expensive materials may be utilized for the pylon members, such as aluminum or extruded nylon, although such materials are heavier.

To enhance the energy storage and release performance of the pylon assembly 12, as more thoroughly described herein, the contiguous surfaces of the cylinders are preferably coated with TEFLON® or SILVERSTONE® coatings fabric, or some similar material to minimize any frictional resistance therebetween.

The pylon 12 further preferably includes energy storage and release means 22. In the preferred embodiment, the energy storage means 22 includes elongated spring elements such as elements 24 and 26, fabricated from the above-described composite materials to provide the necessary energy storage and release, described herein. Those skilled in the art will understand that the invention may be practiced with only one element 24 or 26, or with additional such elements. When a plurality of such elements is utilized, as illustrated in the drawings, they may be assembled in operative relationship with each other through the use of, for example, a nut and bolt combination 28. A protective cap 29 may be provided on the end of the bolt 28.

Figure 6:
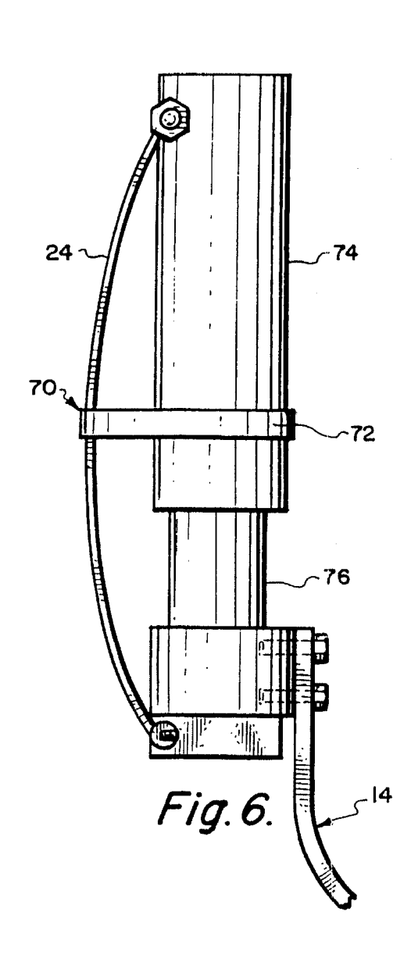
FIG. 6 is a side elevation view of an alternative embodiment of the invention, illustrating the disposition of the lower pylon member internally of the upper pylon member, and further illustrating the use of constraining means in connection with the elongated spring element.
Figure 7:
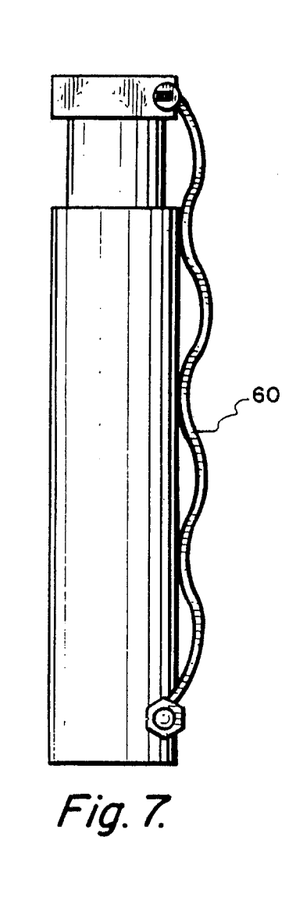
FIGS. 7 and 8 are side elevation views illustrating alternative embodiments of the elongated spring element.
Figure 8:
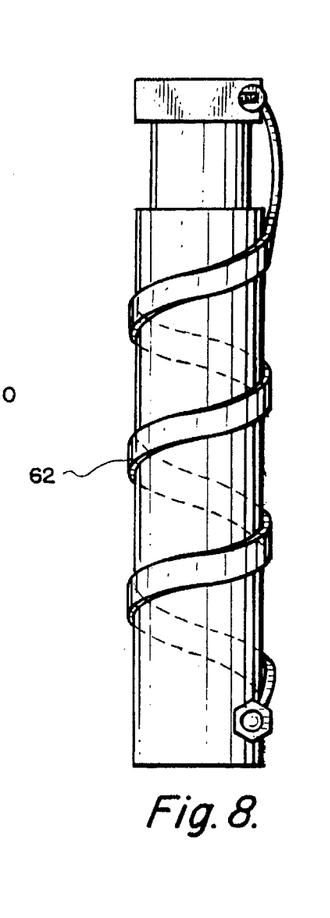

Examples of alternative embodiments of the elongated spring elements 24 and 26 are shown in FIGS. 7 and 8 as elements 60 and 62. Both the multi-curvilinear spring 60 and the helical spring 62 provide the necessary energy performance, and may be utilized in connection with various other spring elements and energy performance structures such as those illustrated in FIGS. 6, 9 and 10, discussed below.

At least one of the preferred spring elements 24 or 26 is operatively connected to the upper and lower pylon portions 18 and 20, such as through the provision of pivotal attachment means 30 and 32. As best shown in FIG. 5, the attachment means 30 and 32 preferably includes tubular cap members 34 and 36 at the respective upper and lower extremities of the spring element 24. The caps 34 and 36 are slidably received in corresponding respective channels 38 and 40, FIG. 4, and retained there by set screws 42, locking nuts 44 or the like.

The caps 34 and 36, as well as the channels 38 and 40, are preferably coated with TEFLON® or SILVERSTONE® coating or similar material to minimize friction therebetween. Among other things, minimizing the friction between these interfaces and between the contacting surfaces of the upper and lower pylon members 18 and 20 (as described above) reduces the loss of energy due to friction during reciprocation of the pylon. Because of the low amount of friction which must be overcome, the prosthesis 10 can provide cushioning and energy-storage, as more fully described below, for even relatively small compressive loads, with relatively low losses of energy due to friction.

Figures 17, 18, 19:
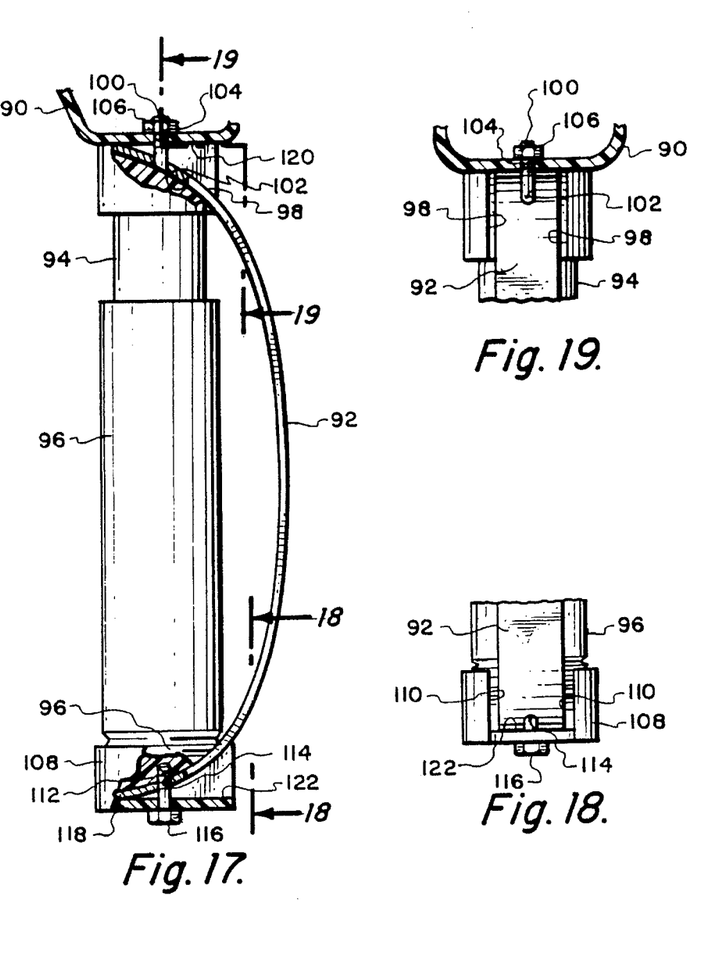
FIG. 17 is a partially sectional, side elevation view of another alternative embodiment of the invention.
FIG. 18 is a partial front elevation view, taken along line
FIG. 19 is a partially sectional, front elevation view, taken along line 19—19 of FIG. 17.

Alternative means for attaching the spring elements 24 and/or 26 to the pylon members 18 and 20 would include, for example, standard hinges (not shown). An example of one of the other many further alternatives for attachment is illustrated in FIGS. 17–19, discussed herein.

Other purposes of the preferred attachment means 30 and 32, in combination with the spring element 24, include the prevention and/or limitation of rotational movement between the respective cylinders 18 and 20. With proper selection of materials and configurations of the cap members 34 and 36 and the spring element 24 (such as size, width, thickness, stiffness and strength of materials), all rotation can be prevented, or some desired and determinable amount of rotation of the lower end of the pylon with respect to the wearer's socket may be permitted. As indicated above, this rotation is similar to that achieved by known prosthetic "rotators". Such rotation is beneficial, and simulates the action of a natural human knee/ankle, in a number of activities that involve the twisting of a person's body with respect to their planted foot, such as golf, tennis, and the like.

By way of example, but not by way of limitation, a wider or stiffer spring element 24 would permit less rotation than a relatively narrower and/or "softer" spring element. Such stiffness of the spring element may be determined, for example, by the number of fiber laminates utilized in the fabrication thereof, if the spring element is fabricated of laminates. If the spring is fabricated from other materials, the particular selection and/or treatment process may be utilized to affect the twisting performance, or the upper and lower pylon members 18 and 20 may be "keyed" to each other to prevent or limit twisting.

In the absence of some control or limitation on such twisting of the cylinders 18 and 20 with respect to each other, such twisting could, for example, cause the lower portion of the prosthesis (in the drawings, the prosthetic foot 14) to become misaligned with respect to the wearer's socket.

As indicated above, the spring elements 24 and 26, as well as other components of the present invention, are preferably formed by the incorporation of a plurality of laminae such as the laminae 58, FIG. 2, embedded in a hardened, flexible polymer, similar to the fabrication methods taught in my above-noted prior art patents. Alternative materials include chopped fiber and thermosetting and/or thermoplastic resins. Such fabrication of the spring elements permits the desired energy storage and release characteristics of the spring, achieving a desired balance between sufficient durability to withstand cyclic loading which may be imposed on the spring and flexibility to cushion impacts of the prosthesis on the ground or other surface and store and release the consequent energy.

The preferred method of manufacturing the spring elements 24 and 26 of the prosthesis 10 is by a thermosetting molding process including the utilization of molds having properly shaped and sized cavities. The cavities are designed to receive the requisite number of laminates and the proper volume of polymer, such that the leg elements 24 and 26 are respectively unitary structures.

Figure 15:
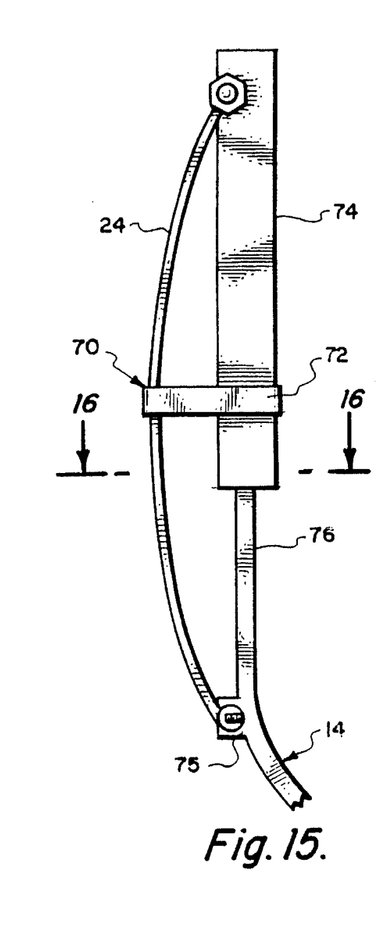
FIG. 15 is a side elevation view of another alternative embodiment of the invention.
Figure 16:
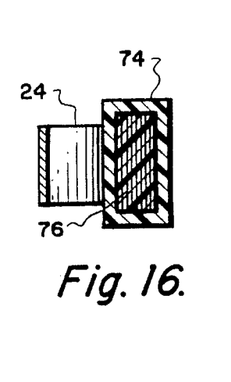
FIG. 16 is a sectional view, taken along line 16—16 of FIG. 15.

As alluded to above, in the preferred embodiment, the lower portion 20 is preferably demountably and adjustably attached to a prosthetic foot 14, although those skilled in the art will understand that the pylon may be utilized in a variety of other manners, such as with a permanently attached or simultaneously- and integrally-formed prosthetic foot member 14 (see, for example, FIGS. 15 and 16 and discussion of same herein). The preferable means for attachment 46 includes a clamp member 48 affixed to the prosthetic foot 14 through the provision of threaded nut and bolt combinations 50, FIGS. 1 and 2, or similar expedient (such as simultaneous formation therewith). In the preferred embodiment, the clamp member 48 may be operably attached at any of a variety of locations along the length of the lower pylon portion 20 by simply positioning the clamp and tightening the nut and bolt combinations 52. This also permits the adjustment of the "toe-in", "toe-out", fore-and-aft alignment of the foot 14 with respect to the socket (see, by way of example, socket 90, FIGS. 17 and 19).

Figures 11, 12, 12A, 13, 14:
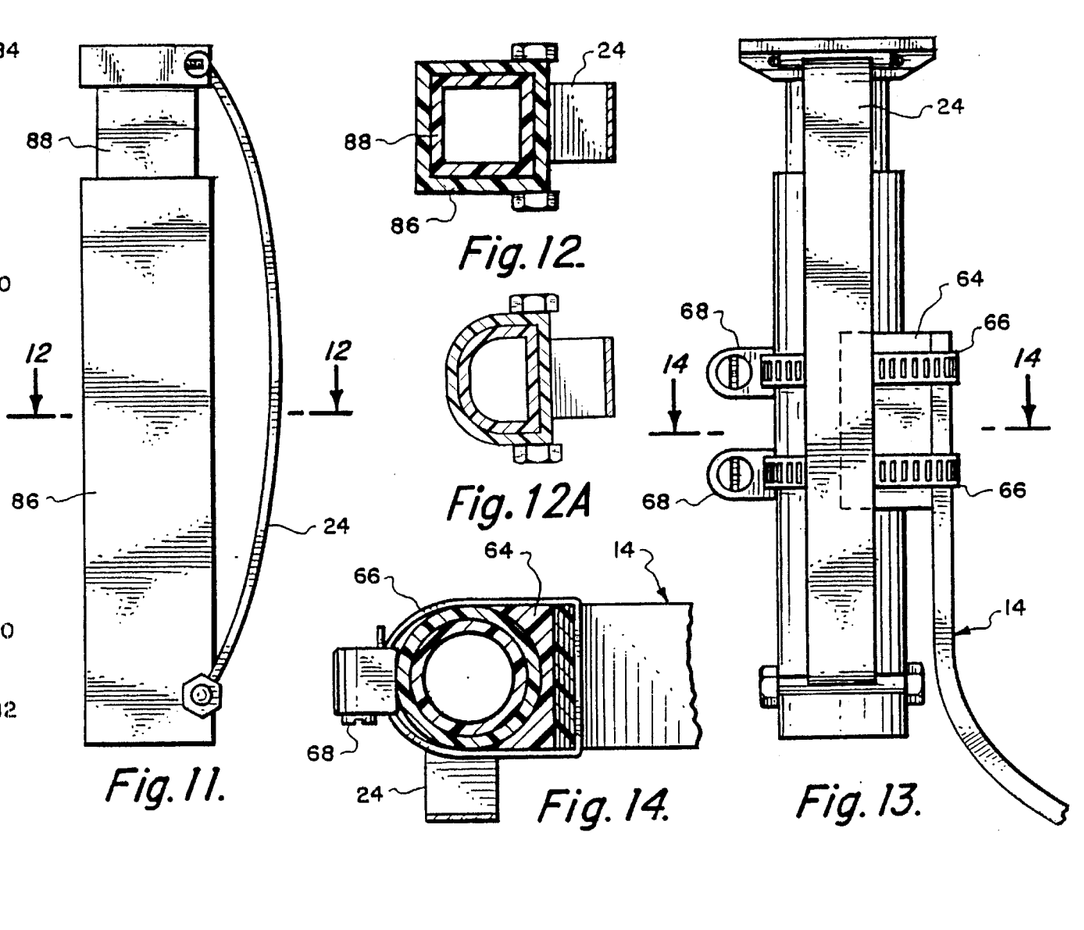
FIG. 11 is a side elevation view of another alternative embodiment of the invention, in which the upper and lower pylon members have a non-circular cross-section.
FIG. 12 is a sectional view, taken along line 12—12 of FIG. 11.
FIG. 12A is a sectional view of an alternative embodiment of the invention taken along line 12—12 of FIG. 11.
FIG. 13 is a side elevation view of another alternative embodiment of the invention, illustrating an alternative means for attaching the lower prosthetic foot to the energy-storing pylon.
FIG. 14 is a sectional view, taken along line 14—14 of FIG. 13.

One of the many alternative means for adjusting and attaching the lower leg prosthesis to the lower pylon is illustrated in FIGS. 13 and 14. The foot prosthesis 14 may be operably retained at a selected position along the length of the lower pylon by one or more hose clamps 66. Presently, it appears that high-strength, heavy duty, wide stainless steel clamps should be utilized. The clamps are adjustable by screws assemblies 68 or similar expedient.

The strength and consequent performance of the attachment of the foot prosthesis 14 may be improved by the provision of a resin or composite wedge 64, FIGS. 13 and 14, formed on the rearward surface of the foot prosthesis 14. The wedge is shaped to conform to the confronting surface of the pylon, and increases the contact area between the foot 14 and the pylon, adding stability to the attachment.

After an amputee has worn the device as illustrated in FIGS. 13 and 14 for some suitable period in order to test the length adjustment and energy performance thereof, the foot 14 may be permanently or semi-permanently bonded in place through the use of known gluing and/or lamination techniques.

Although cap member 29, FIGS. 3 and 4, is shown as contacting the clamp member 48, those skilled in the art will understand that such contact is not required for the practice of the invention. Indeed, and as set forth below, the imposition of force on the pylon 12 will cause the spring element 24 to flex outwardly, away from the pylon portions 18 and 20, correspondingly moving the cap member 29 away from the portions 18 and 20.

A shroud 54 (shown in phantom in FIG. 1) may be provided for a cosmetic finish. Such a shroud may be installed after the judicious adjustment of the prosthesis by the proper combination of elements 18, 20, 24 and/or 26, as well as foot means 14. The shroud should be designed to accommodate and permit the desired flexure and functioning of the prosthesis, without interfering therewith. A shoe 56 or other appropriate covering may also be worn in connection with the assembled prosthesis.

When external forces are applied to the prosthesis 10, such as during walking, running, etc., the forces cause a relative compression of the length of the pylon means 12. As best shown in FIGS. 3 and 4, the first pylon portion 18 will slide downwardly within the second portion 20. Contemporaneously, and as indicated above, the energy storage and release spring elements 24 and 26 will bow outwardly and away from the pylon members 18 and 20.

The amount of compression, and indeed the energy-storage and release characteristics of the prosthetic pylon, will be determined in large part by the construction and materials of the element or elements 24 and 26. Prior to the imposition of such force, the spring elements maintain the lower member 20 in an extended position relative to the upper member 18. When, for example, a contact-generated compressive force is impressed upon the lower member, the lower member 20 will be reciprocated relative to said upper member 18, to compress said storage means into an energy storage mode. When the force is released, the energy storage means will urge the lower member 20 to its extended position.

As illustrated in the drawings, the secondary spring element 26 will not affect the performance of the prosthesis unless and until a sufficiently large compressive force is imposed on the pylon. In such case, the primary spring element 24 will flex to a sufficient degree to permit the secondary element 26 to engage the primary element 24, resulting in a combined resistance to further deflection.

The energy performance of the pylon 12 may be further controlled and/or fine-tuned through the provision of constraining means 70 such as one or more rubber or urethane bands or rings 72, FIG. 6. This band or these bands are preferably dimensioned so that they may be retained about the prosthesis in a position above or below (not shown) the spring element when the prosthesis is in normal use. In this normal position, the band would not affect the energy performance of the prosthesis. In anticipation of heavy impact loading of the prosthesis, however, such as might occur during running or other strenuous exercise, the band 72 may be positioned as illustrated in FIG. 6, so that its elastic resistance to stretching adds to the overall resistance to compression, or "stiffness", of the prosthesis.

FIG. 6 further illustrates an alternative embodiment of the pylon in which an upper pylon member 74 is disposed externally of a lower pylon member 76. In such a configuration, although the foot prosthesis 14 may be selectively positioned along the length of the lower member 76, it must be sufficiently spaced from the upper member 74 to ensure that the desired reciprocation of the pylon members 74 and 76 can occur.

As indicated above, FIGS. 7 and 8 illustrate some of the many alternative embodiments of the elongated spring elements, indicated as elements 60 and 62. As further indicated above, these elements may be utilized in lieu of and/or in combination to the other spring elements and other energy storage means discussed herein (such as, for example, constraining means 70 of FIG. 6).

Figure 9:
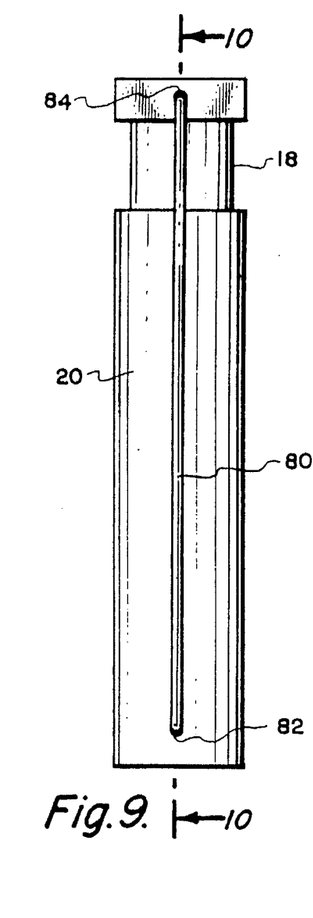
FIG. 9 is a side elevation view of another alternative embodiment of the invention, in which the energy storage means is disposed internally of the upper and lower pylon members.
Figure 10:
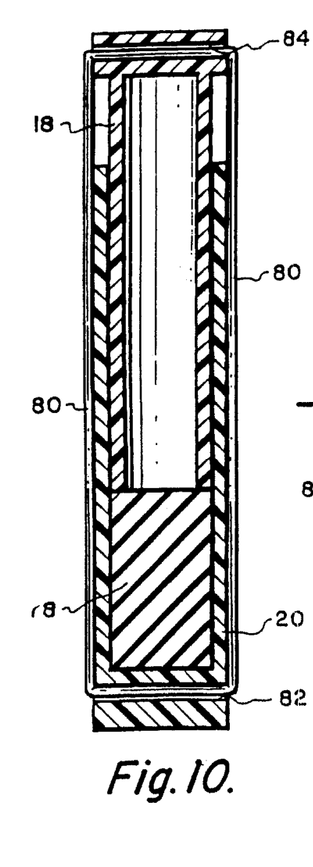
FIG. 10 is a sectional view, taken along line 10—10 of FIG. 9.

FIGS. 9 and 10 illustrate another embodiment of the pylon means 12 of the invention, in which the energy storage means is provided in the form of a resilient, hard rubber rod or inflatable bladder 78. The rod 78 is disposed internally of the lower pylon member 20. The lower end of the upper pylon member 18 is maintained in operative contact with the rod 78 through, for example, the provision of an elastic shock cord 80 or similar expedient. In the embodiment of FIGS. 9 and 10, the shock cord passes through holes 82 and 84 in the lower and upper pylon members, respectively. When compressive loads are imposed on the pylon, the upper member 18 compresses the rubber rod 78; when the load is removed, the rod 78 expands to its original shape and extends the upper member 18 to its original position with respect to the lower member 20.

Another example of the numerous other energy storage means which may be utilized with efficacy in my invention is a plurality of Belville washers (not shown) stacked in an alternating concave/convex manner and disposed internally of the pylon members, similarly to the rubber rod 78. The number of washers in the stack can be selected and varied to adjust the energy-storage and release performance characteristics of the pylon.

FIGS. 11, 12 and 12A illustrate one of the many alternative cross-sections for the upper and lower pylon members. In this embodiment, both the lower member 86 and the upper member 88 incorporate rectangular cross-sections, FIG. 12, which are dimensioned to provide the desired sliding interfitment discussed above.

FIGS. 15 and 16 illustrate an alternative embodiment of my invention, in which a prosthetic foot 14 is integrally formed with the lower pylon member 76. Such an embodiment may incorporate, for example, a slightly modified version of the prosthetic leg and foot sold under the trademark FLEX-FOOT®. Appropriate modifications to that leg and foot would include coating the portion 76 (disposed internally of the sleeve member 74) of the leg with TEFLON® or SILVERSTONE® coatings, or similar low-friction material, and bonding or otherwise attaching the energy-storage means 24 to the foot 14, such as indicated at 75.

FIGS. 17–19 illustrate yet another embodiment of the invention, in which the elongated spring member 92 is operatively connected to the upper pylon member 94 and the lower pylon member 96 in a manner different from those described above.

With respect to the connection between the upper pylon member 94 and the spring 92, a channel 98 is provided in the top portion of the upper pylon member 94. The channel 98 is slightly wider than the spring 92 and the base of the channel is preferably configured so that the upper end of spring member 92 is adjacent thereto when the spring is in a non-compressed state (such as illustrated in FIGS. 17–19). A threaded bolt 100 is operatively mounted (by bonding or similar expedient) in the base of the channel 98 and projects therefrom through a hole 102 in the upper end of spring member 92 and through a hole 104 in the socket member 90. The bolt 100 is preferably threaded only near the outer end of the bolt, in order to engage a nut 106; the remainder of the shaft of the bolt 100 is smooth and may be coated with TEFLON coating or similar material in order to minimize friction during compression of the spring, as more thoroughly described below.

The connection between the lower pylon member 96 and the spring 92 may preferably be assembled in the following manner. A cap member 108 is threadedly engaged on the lower end of the lower pylon member 96. The cap includes an opening 110 in one side, which is sized to permit the spring member 92 to flex during compression of the pylon without contacting the sides of the opening 110. Similarly to the base of the channel 98 described above, the end of the lower pylon member 96 is shaped to conform to the non-compressed spring 92 adjacent thereto. In addition, the end of the lower pylon member 96 includes a threaded hole 112, whose purpose is described below.

To assemble the embodiment of FIGS. 17–19, the lower end of the spring 92 is inserted into the opening 110 and a hole 114 in the spring 92 is positioned between the threaded hole 112 in the bottom of the pylon member 96 and a hole (not shown) in the cap member 108. In order to permit the spring 92 to be fully inserted, the end 118 of the spring 92 is preferably shaped to conform to the confronting annular wall of the cap member 108. A threaded bolt 116 is then inserted through the hole (not shown) in the cap member 108, through the hole 114 in the lower end of the spring element 92, and then threadedly engaged with the hole 112 in the bottom of the pylon member 96. As with the upper bolt 100, the bolt 116 is preferably threaded only on the portion of the bolt that engages the threaded hole 112. The remainder of the bolt 116 is preferably smooth and may be coated with TEFLON coatings or similar material in order to minimize friction during compression of the spring, as described below.

The attachment configuration of FIGS. 17–19 provides numerous advantages. For example, the spring element 92 can be configured with a longer and smoother curvature than that permitted in, for example, the embodiment of FIG. 1. In addition, as the pylon and the spring element 92 are compressed during use, the ends of the spring element 92 will correspondingly move away, respectively, from the curved base of the channel 98 and the curved bottom of the lower pylon member 96, and will move into contact with, respectively, the bottom 120 of the socket 90 and the interior surface 122 of the cap member 108. The area of this contact increases as the compression of the spring 92 increases, and causes an effective shortening of the lever arm by which force is transmitted to the spring. In effect, the spring 92 becomes "stiffer" (exerts a greater resistance to flexure) in proportion to the amount of force exerted thereon. As those skilled in the art will understand, this permits an extremely desirable energy performance, in that the initial loading of the pylon is readily stored by the spring 92, but extreme loading will meet with more "stiffness".

The holes 102 and 114 are preferably sufficiently sized and configured (and may be coated with TEFLON® coating as well) so that, during the compression of the pylon and consequent flexure of the pylon spring element 92, any contact between the holes and their respective bolts 100 and 116 results in minimal frictional energy loss.

By the prosthesis of my invention I provide a leg prosthesis pylon which can be carefully matched to the weight, stride and physical characteristics of the wearer. This is accomplished by carefully selecting and balancing the respective physical characteristics of the energy storage means 22 and the other portions of the pylon.

Moreover, the various components and portions of the present invention may be provided in a variety of sizes, thicknesses, and materials which may be interchangeable with correspondingly-shaped components to permit fine-tuning of the prosthesis to the needs of the wearer thereof. The pylon of my invention may also be used in combination with numerous prior art prosthetic devices to improve the performance of such prior art devices.

The prosthesis of my invention has been described with some particularity but the specific designs and constructions disclosed are not to be taken as delimiting of the invention in that various obvious modifications will at once make themselves apparent to those of ordinary skill in the art, all of which will not depart from the essence of the invention and all such changes and modifications are intended to be encompassed within the appended claims.

I claim:

1. An energy storing lower limb prosthesis, comprising:

a first pylon member having a proximal end and a distal end, said proximal end being attachable to a socket for receiving a stump of an amputee;

a second pylon member also having a proximal end and a distal end, said second pylon member being substantially coaxially aligned with said first pylon member and being further mounted to move axially with respect to said first pylon member;

at least one leaf spring attached to said proximal end of said first pylon member and said distal end of said second pylon member, said leaf spring being capable of storing and releasing energy as said first and second pylon members move axially with respect to one another, and of flexibly controlling the relative axial movement of said first and second pylon members; and a prosthetic foot member secured to said distal end of said second pylon member;

whereby, the energy storage characteristics of said prosthesis in response to vertical compressive loads may be adjusted according to the particular weight and activity level of said amputee by selectively varying the spring characteristics of said leaf spring.

2. The lower limb prosthesis of claim 1, wherein said foot member is adjustably secured to said second pylon member, such that said foot member can be axially and rotationally adjusted relative to said second pylon member.

3. The lower limb prosthesis of claim 1, wherein said foot member has a clamp which can be used to secure said foot member to said second pylon member.

4. The lower limb prosthesis of claim 3, wherein said clamp can be tightened and secured about said second pylon member with at least one nut and bolt member.

5. The lower limb prosthesis of claim 1, wherein said foot member is rotatably secured to said second pylon member to permit the toe-in and toe-out of said foot member to be adjusted.

6. The lower limb prosthesis of claim 1, wherein said leaf spring extends along the side of said first and second pylon members, wherein upon placing a load on said prosthetic foot member, said first and second pylon members slide relative to one another, thereby compressing said leaf spring and causing said leaf spring to deflect outward.

7. The lower limb prosthesis of claim 1, wherein said leaf spring is substantially flat so that it bends about a horizontal axis transverse to said first and second pylon members, and is substantially wide such that it resists any rotational movement between said first and second pylon members.

8. The lower limb prosthesis of claim 1, wherein the ends of said leaf spring are pivotably secured to said first and second pylon members.

9. The lower limb prosthesis of claim 1, wherein said leaf spring is detachably secured to said first and second pylon members.

10. The lower limb prosthesis of claim 1, wherein a retainer is further provided to confine and resist excessive bending of said leaf spring.

11. The lower limb prosthesis of claim 1, wherein a secondary spring member is secured to said leaf spring, said secondary spring member having flexible ends which are adapted to engage said leaf spring as said leaf spring deflects so as to resist excessive bending of said leaf spring.

12. The lower limb prosthesis of claim 1, wherein said first and second pylon members are tubular and have mating cross-sections configured to facilitate relative sliding motion and substantially prevent any relative rotational movement of said first and second pylon members.

13. The lower limb prosthesis of claim 1, wherein said first and second pylon members are constructed of a light weight polymer impregnated fiber material.

14. The lower limb prosthesis of claim 1, wherein at least a portion of the surface between said first and second pylon members is coated with TEFLON® coating.

15. The lower limb prosthesis of claim 1, wherein at least a portion of the surface between said first and second pylon members is coated with SILVERSTONE® coating.

16. The lower limb prosthesis of claim 1, wherein at least a portion of the surface between said first and second pylon members is coated with a low friction material.

17. The lower limb prosthesis of claim 1, wherein said leaf spring is fabricated from superimposed laminates.

18. The lower limb prosthesis of claim 1, wherein said first and second pylon members are tubular in configuration.

19. The lower limb prosthesis of claim 1, wherein said first and second pylon members have a square cross-sectional configuration.

20. The lower limb prosthesis of claim 1, wherein said first and second pylon members have a rectangular cross-sectional configuration.

21. The lower limb prosthesis of claim 1, wherein said first and second pylon members have a D-shaped cross-sectional configuration.

22. The lower limb prosthesis of claim 1, wherein said leaf spring is partially or completely fabricated from a thermo setting resin.

23. The lower limb prosthesis of claim 1, wherein said leaf spring is partially or completely fabricated from a thermo plastic resin.

24. The lower limb prosthesis of claim 1, wherein said leaf spring is partially or completely fabricated from chopped fiber.

25. The lower limb prosthesis of claim 1, wherein said leaf spring is partially or completely fabricated from superimposed laminates.

26. A lower limb prosthesis, comprising:

an upper pylon member;

a lower pylon member reciprocatingly interfitted with said upper pylon member;

at least one elongated leaf spring element attached to both said upper pylon member and said lower pylon member, said spring element extending along said upper and lower pylon members to control the relative axial movement between said upper and lower pylon members, said spring element deflecting relative to said upper and lower pylon members in response to compressive loads incurred during utilization of said prosthesis; and a foot member adjustably secured to said lower pylon member.

27. The lower limb prosthesis of claim 26, in which said upper and lower pylon members are tubular in configuration.

28. The lower limb prosthesis of claim 26, wherein said spring element is substantially flat so that it bends about a horizontal axis transverse to said first and second pylon members, and is substantially wide such that it resists any rotational movement between said upper and lower pylon members.

* * * * *

UNITED STATES PATENT AND TRADEMARK OFFICE
CERTIFICATE OF CORRECTION

PATENT NO.   : 5,458,656
DATED        : October 17, 1995
INVENTOR(S)  : Van L. Phillips It is certified that error appears in the above-indentified patent and that said Letters Patent is hereby corrected as shown below:

On the title page, delete item [73].

Signed and Sealed this

Twenty-third Day of November, 1999

Attest:

Q. TODD DICKINSON

*Attesting Officer*  *Acting Commissioner of Patents and Trademarks*